US005512187A

United States Patent [19]

Buchholz et al.

[11] Patent Number: 5,512,187

[45] Date of Patent: Apr. 30, 1996

[54] METHODS FOR PROCESSING RED CELL PRODUCTS FOR LONG TERM STORAGE FREE OF MICROORGANISMS

[75] Inventors: Donald H. Buchholz, Barrington; Richard L. Kandler, McHenry, both of Ill.

[73] Assignee: Baxter International Inc.

[21] Appl. No.: 299,793

[22] Filed: Sep. 1, 1994

Related U.S. Application Data

[63] Continuation of Ser. No. 167,631, Dec. 14, 1993, abandoned, which is a continuation of Ser. No. 48,074, Apr. 15, 1993, abandoned, which is a continuation of Ser. No. 697,202, May 8, 1991, abandoned.

[51] Int. Cl.[6] ........ B01D 37/00; B01D 36/00

[52] U.S. Cl. ........ 210/767; 210/774; 422/40; 435/2; 604/406; 604/408

[58] Field of Search ........ 210/505, 767, 210/774, 436, 472; 435/2; 604/406, 407, 408, 409, 410; 422/40, 41

[56] References Cited

U.S. PATENT DOCUMENTS

| | | | |
|---|---|---|---|
| 4,330,410 | 5/1982 | Takenaka et al. | 210/767 |
| 4,568,330 | 2/1986 | Kujawski et al. | 604/53 |
| 4,701,267 | 10/1987 | Watanabe et al. | 210/505 |
| 4,767,541 | 8/1988 | Wisdom | 210/787 |
| 4,855,063 | 8/1989 | Carmen et al. | 210/787 |
| 4,880,548 | 11/1989 | Pall et al. | 210/767 |
| 4,917,799 | 4/1990 | Masuda et al. | 210/435 |
| 4,976,685 | 12/1990 | Block, Jr. | 604/52 |
| 4,978,446 | 12/1990 | Lobdell | 210/295 |
| 4,985,153 | 1/1991 | Kuroda et al. | 210/767 |
| 4,997,577 | 3/1991 | Stewart | 210/767 |

FOREIGN PATENT DOCUMENTS 3110022 10/1982 Germany .

OTHER PUBLICATIONS

"Growth of gram-positive and gram-negative bacteria in platelet concentrates", A. Punsalang et al., Transfusion, 1989, vol. 29, No. 7, pp. 596–599.

"Bacterial Proliferation in Platelet Products Stored at Room Temperature (Transfusion-Induced Enterobacter Sepsis)", Buchholz et al., The New England Journal of Medicine, Aug. 19, 1971, vol. 285, No. 8, pp. 430–433.

"Bacterial Properties of Platelet Concentrates", B. Myhre et al., Transfusion, Mar.–Apr. 1974, vol. 14, No. 2, pp. 116–123.

*Primary Examiner*—John Kim

*Attorney, Agent, or Firm*—Daniel D. Ryan; Bradford R. L. Price; Joseph B. Barrett

[57] ABSTRACT

A blood processing method provides a red blood cell product that is free of microorganisms like *Yersinia enterocolitica* during storage periods over 24 hours. The red blood cell product is collected in a first container, where it is refrigerating to cool the blood product to a temperature of about 3 to 5 degrees C. The refrigerated product is transferred from the first container into a storage container through a prescribed filter medium that comprises a mass of synthetic fibers having an average fiber diameter of about 10 microns or less and a bulk density of about 0.7 gram per cubic centimeter or less. The filtered product is retained in the storage container at a temperature of about 3 to 5 degrees C. for a storage period over 24 hours after filtration. Using the filter medium, microorganisms like *Yersinia enterocolitica* present in the red blood cell product at the time of collection are depleted. The filtered blood product remains free of clinically significant numbers of microorganisms throughout refrigerated storage up to time of transfusion.

2 Claims, 2 Drawing Sheets

METHODS FOR PROCESSING RED CELL PRODUCTS FOR LONG TERM STORAGE FREE OF MICROORGANISMS

This is a continuation of copending application Ser. No. 08/167,631 filed on Dec. 14, 1993 now abandoned which is a continuation of application Ser. No. 08/048,074 filed Apr. 15, 1993, now abandoned which is a continuation of application Ser. No. 07/697,202 filed May 8, 1991 (Abandoned).

FIELD OF THE INVENTION

The invention generally relates to blood collection and processing methods. In a more particular sense, the invention relates to methods for removing microorganisms like *yersinia enterocolitica* from red blood cell products prior to long term storage.

BACKGROUND OF THE INVENTION

The published literature reports the presence of small numbers of microorganisms in donor blood at the time of collection. As shown in Table 1, Myhre et al. have detected the presence of from 1 to 8 bacterial strains at the time of phlebotomy, with some strains being present at concentrations greater than 25 organisms per ml. Myhre et al., "Bacteriocidal Properties of Platelet Concentrates," *Transfusion* 14:116 (1974).

TABLE 1

Organisms Isolated From the First 7 mL of Donated Blood From Nine Normal Donors

| Bacteria | Occurrence (N = 9) | Bacterial Concentration (org/ml) |
|---|---|---|
| Diptheroid sp. | 1 | 10 colonies/7 ml |
| Staph. epid. | 6 | 1–200+ |
| Bacillus sp. | 9 | 1–200+ |
| Micrococcus | 1 | 4 |
| Staph. aureus | 4 | 1–100+ |
| Neisseria sp. | 2 | 1–100+ |
| alpha. strep. | 2 | 2–100+ |
| Staph. sp. | 1 | 1 |

While there may be bacteria present at the time of blood collection, the presence of clinically significant numbers of bacteria at the time of transfusion is rarely encountered. For many years, this decline in the number of bacteria in donor blood between time of collection and the time of transfusion has been attributed to a sterilizing activity of white blood cells and plasma factors. See, for example, Buchholz et al , "Bacteria Proliferation in Platelet Products Stored at Room Temperature," *NEJM* 285:429 (1971); and Punsalang et al , "Growth of Gram-Positive and Gram-Negative Bacteria in Platelet Concentrates," *Transfusion* 29:596 (1989)

The occurrence of transfusion-induced sepsis is considered less likely with stored red blood cells (which are refrigerated during storage at about 4 degrees C.), compared to platelet concentrates (which are stored at room temperature). Still, there have been reports of sepsis caused by transfusions of refrigerated red blood cells with the organism *Yersinia enterocolitica* (which will be referred to as "Yersinia"). Yersinia is a human pathogen that can multiple in blood even during refrigerated storage at 4 degrees C. The occurrence of sepsis due to the presence of Yersinia in stored blood products is very rare, with only about twenty-three cases reported in the United States in the last nine years.

Still, it would be desirable to completely eliminate its occurrence altogether.

SUMMARY OF THE INVENTION

The invention provides blood processing methods that significantly reduce the presence of microorganisms like Yersinia in stored red blood cell products.

The method that embodies the features of the invention collects a blood product containing red blood cells in a first container that forms a part of a sterile, closed blood collection system. The method refrigerates the blood product in the first container to cool the blood product to a temperature of about 3 to 5 degrees C. The refrigerated blood product is transferred from the first container into a storage container using a sterile, closed transfer system that includes an inline filter medium comprising a mass of synthetic fibers having an average fiber diameter of about 10 microns or less and a bulk density of about 0.7 gram per cubic centimeter or less. The method stores the filtered blood product in the storage container at a temperature of about 3 to 5 degrees C. for at least twenty-four hours after filtration for subsequent transfusion.

The inventors have discovered that, by following the prescribed method, clinically significant amounts of microorganisms like Yersinia that can be present in the red blood cell product at the time of collection can be virtually eliminated. The prescribed method provides a red blood cell product that is free of clinically significant amounts of microorganisms at the beginning of the storage period. The microorganism-depleted condition persists throughout the storage period up to the time of transfusion.

The discovery is surprising and unexpected. At the present time, the inventors do not know exactly why or how the invention achieves the benefits it does.

It is known that the filter medium used in the prescribed processing method serves to remove essentially all the leukocytes from the whole blood and red blood cell products. Since leukocytes are thought to scavenge microorganisms present in stored blood products, conventional wisdom would expect an increase in the number of microorganisms in the filtered, leuko-depleted red blood cell product during storage for over twenty-four hours. Surprisingly, the inventors have found the reverse to be true. The filtered red blood cell product remains free of clinically significant amounts of microorganisms for storage periods well in excess of twenty-four hours, despite also being in a leuko-depleted condition.

Other features and advantages of the invention will become apparent upon review of the following description, drawings, and appended claims.

DESCRIPTION OF THE PREFERRED EMBODIMENTS

Figure 1:
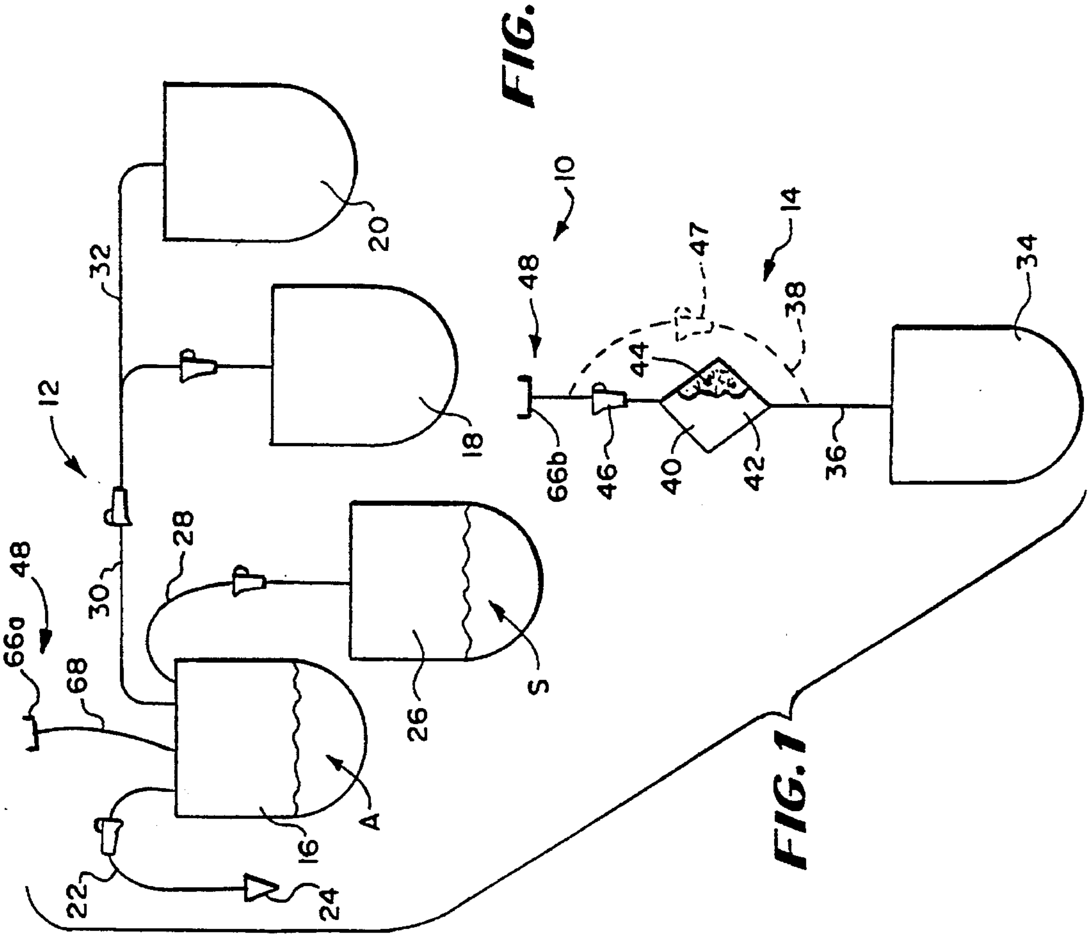
FIG. 1 is a schematic view of a blood collection system that includes a blood processing assembly and a blood transfer assembly that embody the features of the invention.

A blood collection system 10 is shown in FIG. 1. The system 10 comprises a blood collection, processing and storage assembly 12 and a transfer assembly 14.

In the illustrated and preferred embodiment shown in FIG. 1, the transfer assembly 14 comprises an initially separate subassembly not joined to the blood processing assembly 12. It should be appreciated, however, that the transfer assembly 14 can be made as an integral part of the processing assembly 12.

The blood collection assembly 12 comprises a multiple blood bag system having a primary bag or container 16 and one or more integrally attached transfer bags or containers 18 and 20. In use, the primary bag 16 (which is typically also called a donor bag) receives whole blood from a donor through integrally attached donor tubing 22 that carries an phlebotomy needle 24. A suitable anticoagulant A is contained in the primary bag 16.

A satellite bag 26 is attached to the primary bag 16 by integrally attached tubing 28. The satellite bag 26 contains a suitable storage solution S for red blood cells. One such solution is disclosed in Grode et al U.S. Pat. No. 4,267,269.

The transfer bags 18 and 20 are attached to the primary bag 16 by integrally attached transfer tubing 30 and 32. The transfer bags 18 and 20 are intended to receive the platelet and plasma blood components for processing. The first transfer bag 18 ultimately serves as the storage container for the platelet concentrate, and the second transfer bag 20 ultimately serves as the storage container for the platelet-poor plasma.

All of the bags and tubing associated with the processing assembly 12 can be made from conventional approved medical grade plastic materials, such as polyvinyl chloride plasticized with di-2-ethylhexylphthalate (DEHP). Alternatively, the first transfer container 18, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTH). These materials, when compared to DEHP-plasticized polyvinyl chloride materials, have greater gas permeability that is beneficial for platelet storage.

The blood collection assembly 12, once sterilized, constitutes a sterile, "closed" system, as judged by the applicable standards in the United States.

Whole blood is collected and then separated into its various therapeutic components within the assembly 12. These therapeutic components are typically red blood cells, plasma, and platelets. In use, the collected whole blood is centrifugally separated within the primary bag 16 into red blood cells and platelet-rich plasma. The platelet-rich plasma is transferred by conventional techniques into the first transfer bag 30, leaving the red blood cells in the primary bag. The transfer bags 18 and 20 are detached in a sterile fashion using a conventional heat sealing device (for example, the Hematron® dielectric sealer sold by Baxter Healthcare Corporation), which forms a hermetic, snap-apart seal in the tubing 30 (this seal is schematically shown by an "x" in FIGS. 2 and 3).

Figure 2:
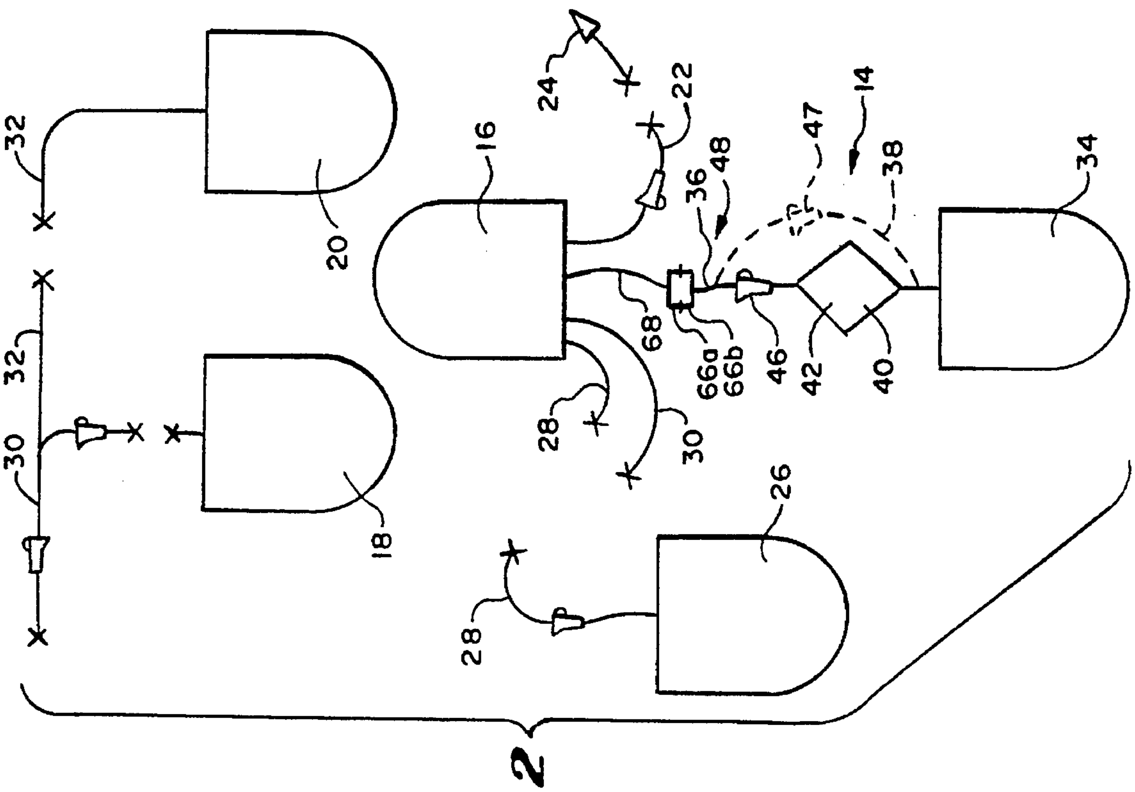
FIG. 2 is a schematic view of the system shown in FIG. 1, with the blood transfer assembly attached to the blood processing assembly for the purpose of removing undesired matter from the blood cells.

The red blood cell storage solution S is transferred into the primary container 16, and the satellite bag 26 is then disconnected using the snap-apart seal "x" (as shown in FIG. 2). The donor tubing 22 is also sealed and disconnected in the same fashion (as also shown in FIG. 2).

The platelet-rich plasma can undergo subsequent centrifugal separation within the first transfer bag 18 into platelet concentrate and platelet-poor plasma. The platelet-poor plasma is transferred into the second transfer bag 20, leaving the platelet concentrate in the first transfer bag 18. The transfer bags 18 and 20 are then separated by the snap-apart seals "x" in the tubing 32 (as shown in FIG. 2) for subsequent storage of the collected components.

The transfer assembly 14 includes a storage container 34 and an associated fluid flow path 36. An optional air vent path 38 is also provided (shown in phantom lines in FIG. 1 to 3). The transfer assembly 14 includes a conventional roller clamp 46 associated with the flow path 36. The transfer assembly 14 also includes a conventional roller clamp 47 associated with the optional air vent path 38.

The transfer container 34 and fluid paths 36 and 38 are all made of low cost medical grade plastic materials, such as polyvinyl chloride plasticized with DEHP.

The fluid path 36 includes an inline filtration device 40 for separating undesired matter from refrigerated whole blood and other refrigerated blood products that contain red blood cells.

In the illustrated embodiment, the filtration device 40 includes a housing 42 containing a filtration medium 44. The filtration medium 44 comprises a mass of synthetic fibers having a average fiber diameter of about 10 microns or less and a bulk density of about 0.7 gram per cubic centimeter or less. Filtration mediums of this type are described in Takenaka et al. U.S. Pat. No. 4,330,410 and Watanabe et al U.S. Pat. No. 4,701,267, both of which are incorporated herein by reference. Filters having filter mediums of this type are also commercially available and sold by the Fenwal Division of Baxter Healthcare Corporation under the tradename Sepacell R-500 Leukodepletion Filters.

In the illustrated and preferred embodiment, a connection assembly 48 is associated with the initially separate blood collection and transfer assemblies 12 and 14. The connection assembly 48 permits selective attachment of the transfer assembly 14 to the blood collection assembly 12. Once attached with the flow control device 46 opened (and optional flow control device 47 closed) (as shown in FIG. 2), red blood cells can be conveyed from the primary container 16 through the flow path 36 and filtration device 40 into the storage container 34.

While the two assemblies 12 and 14 are still attached together, the flow control device 46 can be closed and optional flow control device 47 opened to vent entrapped air from the storage container 34 through the vent path 38 into the primary container 16.

Figure 3:
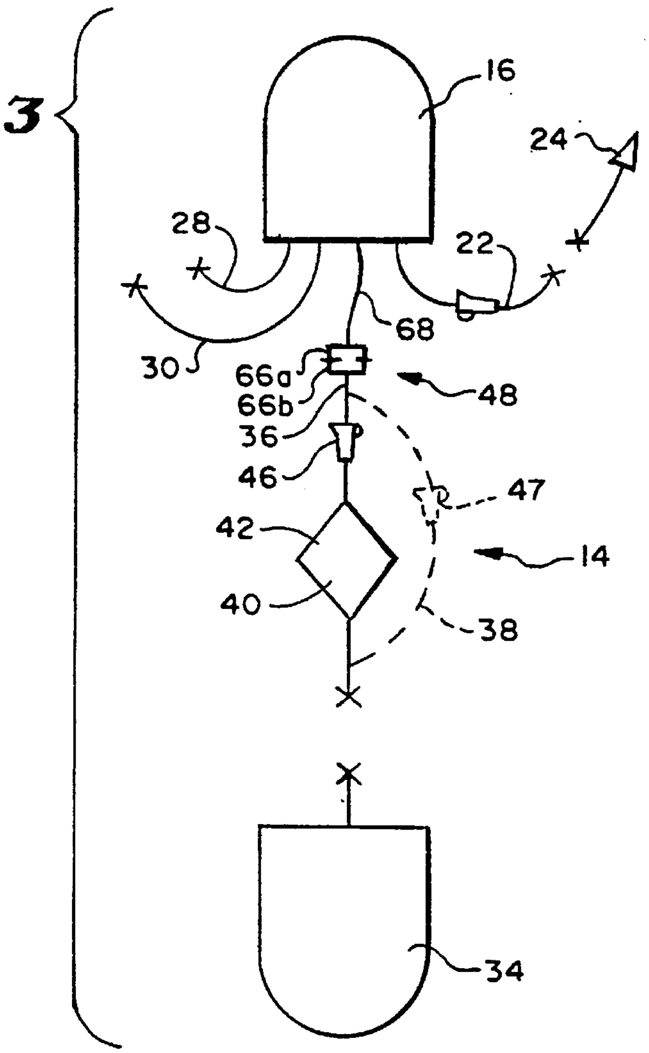
FIG. 3 is a schematic view of the system shown in FIG. 1, with the blood cells, now substantially free of undesired matter, ready for long term storage.

The storage container 34 is then detached from the transfer assembly 14, as shown in FIG. 3. The filtered red blood cell blood product is stored in the separated container 34.

In the illustrated and preferred embodiment, the filtration assembly 14, once sterilized, comprises a sterile, "closed" system (like the processing and storage assembly 12), as judged by the applicable United States standards. In this arrangement, the connection assembly 48 serves to attach and detach the collection and filtration assembly in a manner that preserves the sterile integrity of the closed systems 12 and 14.

More particularly, the connection assembly 48 comprises two mating sterile connection devices (designated 66*a* and 66*b* ). The devices 66*a* and 66*b* (see also FIG. 4) are described in Granzow et al U.S. Pat. Nos. 4,157,723 and 4,265,280, which are incorporated herein by reference. One device 66*a* is carried by tubing 68 attached to the primary bag 16. The other device 66*b* is carried at the end 54 of the flow path 36 of the transfer assembly 14.

Figure 4:
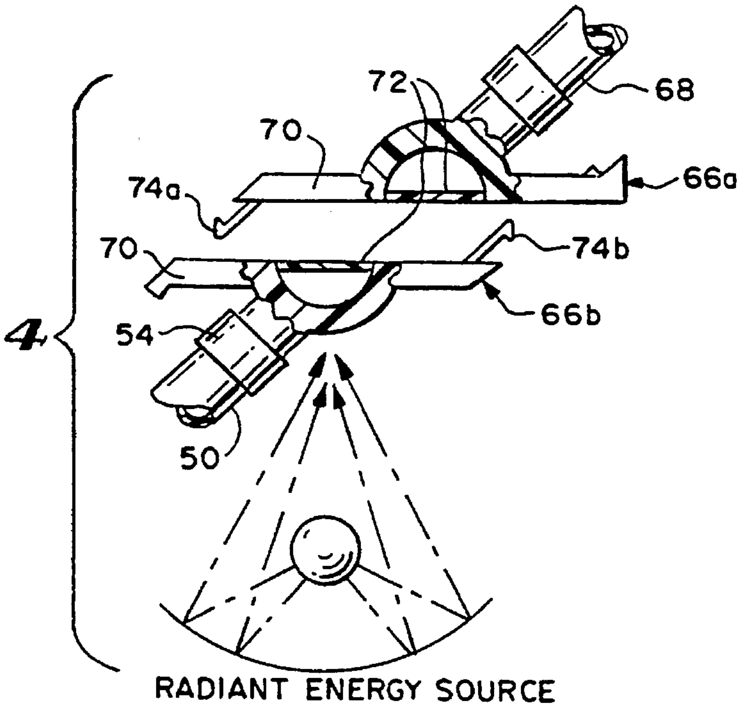
FIG. 4 is an enlarged side sectional view of the sterile connection devices associated with the system shown in FIG. 1.

As shown in FIG. 4, the sterile connection devices 66*a* and 66*b* each generally includes a housing 70 having a normally closed, meltable wall 72 made of a radiant energy absorbing material. The housings 70 are joined together with mating bayonet-type couplers 74*a* and 74*b*, with the walls 72 placed in facing contact. When connected and exposed to radiant energy, the walls 72 melt at temperatures that result in the destruction of bacteria, while at the same time opening a fluid path between the connected housings 70.

The devices 66*a* and 66*b* normally close the associated assemblies 12 and 14 from communication with the atmosphere and are opened in conjunction with an active sterilization step which serves to sterilize the regions adjacent to the interconnecting fluid path as the fluid path is being formed. These devices 66*a* and 66*b* also hermetically seal the interconnecting fluid path at the time it is formed. The use of these sterile connection devices 66*a* and 66*b* assures a probability of non-sterility that exceeds one in a million. The devices 66*a* and 66*b* thus serve to connect the two assemblies 12 and 14 without compromising the sterile integrity of either.

Alternately, the connection assembly 48 can comprise the sterile connecting system disclosed in Spencer U.S. Pat. No. 4,412,835 (not shown). In this arrangement, this system forms a molten seal between the transfer tubing 30 of the primary bag 16 with the tubing end portion 54 of the filtration assembly 14. Once cooled, a sterile weld is formed.

It is known that the just described filtration medium 44 is suited for the removal of white blood cells and platelets from refrigerated whole blood and red blood cells. The inventors have discovered that the filtration medium 44 also removes microorganisms like Yersinia from refrigerated red blood cell products prior to long term storage. This microorganism-depleted condition the invention provides persists during long term storage of red blood cell products at temperatures of about 3 to 5 degrees for periods well over twenty-four hours.

In use, whole blood is collected in the donor bag 16, which forms a part of the blood collection assembly 12. After removal of the platelet-rich plasma and detachment of the transfer bags (see FIG. 2), the red blood cells remain in the donor bag 16. The storage solution S is conveyed from the bag 26 into the donor bag 16, and the bag 26 is disconnected. The resulting red blood cell product is refrigerated in the donor bag 16 to cool the product to a temperature of about 3 to 5 degrees C.

Following refrigeration, the donor bag 16 is attached to the transfer assembly 14 using the associated sterile connection devices 66*a* and 66*b*. The roller clamp 46 is opened, and the roller clamp 47 is closed.

As shown in FIG. 2, the donor bag 16 is lifted above the storage bag 34, and the refrigerated red blood cells are conveyed by gravity flow from the donor bag 16 through the fluid path 36 and filtration device 40 and into the storage bag 34. Microorganisms are removed from the red blood cells by the filtration device 40. Leukocytes are also removed in the process.

Should air be trapped in the storage bag 34, it may be necessary to transfer the air through the vent path 38 into the donor bag 16 in the manner previously described.

The storage bag 34 is then separated from the transfer assembly 14. This is accomplished by forming snap-apart seals "x" in the tubing 36 of the transfer assembly 14 (as FIG. 3 shows).

The leukocyte-depleted red blood cell product, now substantially free of microorganisms like Yersinia, is stored in the storage bag 34 at temperatures of from 3 to 5 degrees C. for a period over twenty-four hours before transfusing.

The following example demonstrates the surprising and unexpected results of the invention.

EXAMPLE

Units of whole blood were collected from different donors in separate sterile, closed multiple blood bag systems, like that shown in FIG. 1. Within thirty minutes of collection, test units were prepared using aseptic conditions. Each test unit was made by pooling two units of ABO-compatible whole blood from two different donors. These test units are identified as Pools A through L in the Result Tables 2 to 5 below.

The Pools of whole blood were inoculated with Yersinia at four different inoculation levels: at about 1 organism per ml (Pools A, B, and C); at about 2 to 3 organisms per ml (Pools D, E, and F); at about 30 organisms per ml (Pools G, H, and I); and at about 135 organisms per ml (Pools J, K, and L). Each inoculated pooled test unit was mixed well.

It is believed that the inoculation levels of below 10 organisms per ml. represent amounts of Yersinia that could be present in the blood of an asymptomatic or otherwise apparently healthy prospective donor. Due to the lack of atypical symptoms, these persons would be permitted to join the pool of prospective blood donors. Therefore, it is possible that blood containing Yersinia at these asymptomatic levels could be collected.

It is believed that the higher inoculation levels of more than 10 organisms per ml represent amounts of Yersinia that, if present in the blood of a prospective donor, would manifest itself as fever or other atypical physical symptoms. The atypical symptoms would be detected during routine pre-collection examination, eliminating these symptomatic persons from the pool of prospective blood donors. Therefore, it is unlikely that blood containing Yersinia at these high, symptomatic levels would be collected.

After mixing, each inoculated Pool of whole blood was broken into single unit pairs (referred to as Units A and B in the Result Tables below). Each unit pair was sampled for quantitative culture (as shown in the "Pre-Hold" column of the Results Table). The inoculated Unit pairs for Pool were held for seven hours at room temperature and again sampled for quantitative culture (as shown in the "Pst-Hold" column of the Results Table).

Each inoculated Unit pair of whole blood was processed into platelet-rich plasma and red blood cells in the manner described in this Specification. The red blood cell storage solution described in Grode et al U.S. Pat. No. 4,267,269 was added to the red blood cells in each Unit pair.

The resulting red blood cell product for each inoculated Unit pair were refrigerated for 18 to 24 hours to a temperature of 4 degrees C. The red blood cells for each inoculated Unit pair where then sampled for quantitative culture (as shown in the "PreFilt Day 1" column of the Results Table).

Unit A of each red blood cell product pair was transferred into another storage container via the inline filtration device described above. Red blood cell product Unit A were sampled after filtration for quantitative culture (as shown in the "PstFilt Day 1" column of the Results Table). The Units A were then stored at 3 to 5 degrees C. Quantitative cultures were obtained at the end of 7, 14, 21, 28, 35, and 42 days of storage (as shown in the Day columns in the Results Table).

Unit B of each red blood cell product pair was stored as a control without undergoing filtration at 3 to 5 degrees C. Quantitative cultures were obtained at the end of 7, 14, 21, 28, 35, and 42 days of storage (as shown in the Day columns in the Result Tables).

The results of the study are summarized in the following Results Tables 2 to 5.

TABLE 2

TEST RESULT

INOCULATION LEVEL - about 1 org/mL

| | | Broth Control | | | CULTURE RESULTS | | | | | | | | | |
|---|---|---|---|---|---|---|---|---|---|---|---|---|---|---|
| | | | | | Whole Blood (org/mL) | | PreFitt | PstFitt | | Red Cells (org/mL) | | | | |
| | repl | (org/mL) | | repl | Pre-Hold | Pst-Hold | Day 1 | Day 1 | Day 7 | Day 14 | Day 21 | Day 28 | Day 35 | Day 42 |
| Pool A | a | .787 | Unit "A" | a | 0.0 | 0.0 | 0.0 | 0.0 | 0.0 | 0.0 | 0.0 | 0.0 | 0.0 | 0.0 |
| | b | .733 | | b | 0.0 | 0.0 | 0.0 | 0.0 | 0.0 | 0.0 | 0.0 | 0.0 | 0.0 | 0.0 |
| | c | .741 | | c | 0.0 | 0.0 | 0.0 | 0.0 | 0.0 | 0.0 | 0.0 | 0.0 | 0.0 | 0.0 |
| | | | Unit "B" | a | 0.0 | 0.0 | 0.0 | NA | 0.0 | 557 | conf | conf | conf | conf |
| | | | unfiltered | b | 0.0 | 0.0 | 0.0 | NA | 2.0 | 438 | conf | conf | conf | conf |
| | | | | c | 0.0 | 0.0 | 0.0 | NA | 1.0 | 732 | conf | conf | conf | conf |
| Pool B | a | .787 | Unit "A" | a | 0.0 | 0.0 | 0.0 | 0.0 | 0.0 | 0.0 | 0.0 | 0.0 | 0.0 | 0.0 |
| | b | .733 | | b | 0.0 | 0.0 | 0.0 | 0.0 | 0.0 | 0.0 | 0.0 | 0.0 | 0.0 | 0.0 |
| | c | .741 | | c | 0.0 | 0.0 | 0.0 | 0.0 | 0.0 | 0.0 | 0.0 | 0.0 | 0.0 | 0.0 |
| | | | Unit "B" | a | 0.0 | 0.0 | 0.0 | NA | 0.0 | 22 | tntc | conf | conf | conf |
| | | | unfiltered | b | 0.0 | 0.0 | 0.0 | NA | 1.0 | 30 | tntc | conf | conf | conf |
| | | | | c | 0.0 | 0.0 | 0.0 | NA | 0.0 | 28 | tntc | conf | conf | conf |
| Pool C | a | .787 | Unit "A" | a | 0.0 | 0.0 | 0.0 | 0.0 | 0.0 | 0.0 | 0.0 | 0.0 | 0.0 | 0.0 |
| | b | .733 | | b | 0.0 | 0.0 | 0.0 | 0.0 | 0.0 | 0.0 | 0.0 | 0.0 | 0.0 | 0.0 |
| | c | .741 | | c | 0.0 | 0.0 | 0.0 | 0.0 | 0.0 | 0.0 | 0.0 | 0.0 | 0.0 | 0.0 |
| | | | Unit "B" | a | 0.0 | 0.0 | 0.0 | NA | 0.0 | 0.0 | 0.0 | 0.0 | 0.0 | 0.0 |
| | | | unfiltered | b | 0.0 | 0.0 | 0.0 | NA | 0.0 | 0.0 | 0.0 | 0.0 | 0.0 | 0.0 |
| | | | | c | 0.0 | 0.0 | 0.0 | NA | 0.0 | 0.0 | 0.0 | 0.0 | 0.0 | 0.0 |

tntc - too numerous to count
conf - confluent growth
NA - Not Applicable

TABLE 3

TEST RESULT

INOCULATION LEVEL - about 2–3 org/mL

| | | Broth Control | | | CULTURE RESULTS | | | | | | | | | |
|---|---|---|---|---|---|---|---|---|---|---|---|---|---|---|
| | | | | | Whole Blood (org/mL) | | PreFitt | PstFitt | | Red Cells (org/mL) | | | | |
| | repl | (org/mL) | | repl | Pre-Hold | Pst-Hold | Day 1 | Day 1 | Day 7 | Day 14 | Day 21 | Day 28 | Day 35 | Day 42 |
| Pool D | a | 2.9 | Unit "A" | a | 0.0 | 0.0 | 0.0 | 0.0 | 0.0 | 0.0 | 0.0 | 0.0 | 0.0 | 0.0 |
| | b | 3.3 | | b | 0.0 | 0.0 | 0.0 | 0.0 | 0.0 | 0.0 | 0.0 | 0.0 | 0.0 | 0.0 |
| | c | 2.5 | | c | 0.0 | 0.0 | 0.0 | 0.0 | 0.0 | 0.0 | 0.0 | 0.0 | 0.0 | 0.0 |
| | | | Unit "B" | a | 0.0 | 0.0 | 0.0 | NA | 4.0 | tntc | conf | conf | conf | conf |
| | | | unfiltered | b | 0.0 | 0.0 | 0.0 | NA | 1.0 | tntc | conf | conf | conf | conf |
| | | | | c | 0.0 | 0.0 | 0.0 | NA | 5.0 | tntc | conf | conf | conf | conf |
| Pool E | a | 2.9 | Unit "A" | a | 0.0 | 0.0 | 0.0 | 0.0 | 0.0 | 0.0 | 0.0 | 0.0 | 0.0 | 0.0 |
| | b | 3.3 | | b | 0.0 | 0.0 | 0.0 | 0.0 | 0.0 | 0.0 | 0.0 | 0.0 | 0.0 | 0.0 |
| | c | 2.5 | | c | 0.0 | 0.0 | 4.0 | 0.0 | 0.0 | 0.0 | 0.0 | 0.0 | 0.0 | 0.0 |
| | | | Unit "B" | a | 0.0 | 0.0 | 0.0 | NA | 7.0 | tntc | conf | conf | conf | conf |
| | | | unfiltered | b | 0.0 | 0.0 | 0.0 | NA | 5.0 | tntc | conf | conf | conf | conf |
| | | | | c | 1.0 | 0.0 | 0.0 | NA | 4.0 | tntc | conf | conf | conf | conf |
| Pool F | a | 2.9 | Unit "A" | a | 0.0 | 0.0 | 0.0 | 0.0 | 0.0 | 0.0 | 0.0 | 0.0 | 0.0 | 0.0 |
| | b | 3.3 | | b | 0.0 | 0.0 | 0.0 | 0.0 | 0.0 | 0.0 | 0.0 | 0.0 | 0.0 | 0.0 |
| | c | 2.5 | | c | 0.0 | 0.0 | 0.0 | 0.0 | 0.0 | 0.0 | 0.0 | 0.0 | 0.0 | 0.0 |
| | | | Unit "B" | a | 0.0 | 0.0 | 0.0 | NA | 0.0 | 2.0 | 394 | tntc | conf | conf |
| | | | unfiltered | b | 0.0 | 0.0 | 0.0 | NA | 0.0 | 1.0 | 340 | tntc | conf | conf |
| | | | | c | 0.0 | 0.0 | 0.0 | NA | 0.0 | 3.0 | 376 | tntc | conf | conf |

TABLE 3-continued

| | | | | | TEST RESULT | | | | | | | | | |
|---|---|---|---|---|---|---|---|---|---|---|---|---|---|---|
| INOCULATION LEVEL - about 2–3 org/mL | | | | | CULTURE RESULTS | | | | | | | | | |
| | | Broth Control | | | Whole Blood (org/mL) | | PreFitt | PstFitt | | Red Cells (org/mL) | | | | |
| | repl | (org/mL) | | repl | Pre-Hold | Pst-Hold | Day 1 | Day 1 | Day 7 | Day 14 | Day 21 | Day 28 | Day 35 | Day 42 |

tntc - too numerous to count
conf - confluent growth
NA - Not Applicable

TABLE 4

| | | | | | TEST RESULT | | | | | | | | | |
|---|---|---|---|---|---|---|---|---|---|---|---|---|---|---|
| INOCULATION LEVEL - about 30 org/mL | | | | | CULTURE RESULTS | | | | | | | | | |
| | | Broth Control | | | Whole Blood (org/mL) | | PreFitt | PstFitt | | AS-1 Red Cells (org/mL) | | | | |
| | repl | (org/mL) | | repl | Pre-Hold | Pst-Hold | Day 1 | Day 1 | Day 7 | Day 14 | Day 21 | Day 28 | Day 35 | Day 42 |
| Pool G | a | 29.2 | Unit "A" | a | 0.0 | 0.0 | 0.0 | 0.0 | 1.0 | 0.0 | 0.0 | 0.0 | | |
| | b | 30.6 | | b | 0.0 | 0.0 | 0.0 | 0.0 | 0.0 | 0.0 | 0.0 | 0.0 | | |
| | c | 34.7 | | c | 0.0 | 0.0 | 0.0 | 0.0 | 1.0 | 0.0 | 0.0 | 0.0 | | |
| | | | Unit "B" | a | 0.0 | 0.0 | 0.0 | NA | 6.0 | 960 | conf | conf | | |
| | | | unfiltered | b | 0.0 | 0.0 | 0.0 | NA | 3.0 | 1269 | conf | conf | | |
| | | | | c | 0.0 | 0.0 | 0.0 | NA | 4.0 | 1153 | conf | conf | | |
| Pool H | a | 29.2 | Unit "A" | a | 0.0 | 0.0 | 1.0 | 0.0 | 0.0 | 0.0 | 0.0 | 0.0 | | |
| | b | 30.6 | | b | 0.0 | 0.0 | 0.0 | 0.0 | 0.0 | 0.0 | 0.0 | 0.0 | | |
| | c | 34.7 | | c | 0.0 | 0.0 | 1.0 | 0.0 | 0.0 | 0.0 | 0.0 | 0.0 | | |
| | | | Unit "B" | a | 3.0 | 0.0 | 1.0 | NA | 83 | tntc | conf | conf | | |
| | | | unfiltered | b | 0.0 | 0.0 | 1.0 | NA | 104 | tntc | conf | conf | | |
| | | | | c | 1.0 | 0.0 | 0.0 | NA | 127 | tntc | conf | conf | | |
| Pool I | a | 29.2 | Unit "A" | a | 5.0 | 0.0 | 6.0 | 0.0 | 0.0 | 0.0 | 0.0 | 0.0 | | |
| | b | 30.6 | | b | 2.0 | 0.0 | 1.0 | 0.0 | 0.0 | 0.0 | 0.0 | 0.0 | | |
| | c | 34.7 | | c | 2.0 | 1.0 | 1.0 | 0.0 | 0.0 | 0.0 | 0.0 | 0.0 | | |
| | | | Unit "B" | a | 1.0 | 0.0 | 3.0 | NA | tntc | conf | conf | conf | | |
| | | | unfiltered | b | 4.0 | 1.0 | 1.0 | NA | tntc | conf | conf | conf | | |
| | | | | c | 2.0 | 0.0 | 1.0 | NA | tntc | conf | conf | conf | | |

tntc - too numerous to count
conf - confluent growth
NA - Not Applicable

TABLE 5

| | | | | | TEST RESULT | | | | | | | | | |
|---|---|---|---|---|---|---|---|---|---|---|---|---|---|---|
| INOCULATION LEVEL - about 100 org/mL | | | | | CULTURE RESULTS | | | | | | | | | |
| | | Broth Control | | | Whole Blood (org/mL) | | PreFitt | PstFitt | | AS-1 Red Cells (org/mL) | | | | |
| | repl | (org/mL) | | repl | Pre-Hold | Pst-Hold | Day 1 | Day 1 | Day 7 | Day 14 | Day 21 | Day 28 | Day 35 | Day 42 |
| Pool J | a | 139.6 | Unit "A" | a | 1.0 | 0.0 | 2.0 | 0.0 | 0.0 | 0.0 | 0.0 | | | |
| | b | 133.7 | | b | 0.0 | 0.0 | 0.0 | 0.0 | 0.0 | 0.0 | 0.0 | | | |
| | c | 134.4 | | c | 1.0 | 0.0 | 0.0 | 0.0 | 0.0 | 0.0 | 0.0 | | | |
| | | | Unit "B" | a | 0.0 | 0.0 | 1.0 | NA | 3.0 | 75 | tntc | | | |
| | | | unfiltered | b | 1.0 | 1.0 | 0.0 | NA | 0.0 | 69 | tntc | | | |
| | | | | c | 0.0 | 0.0 | 0.0 | NA | 0.0 | 70 | tntc | | | |
| Pool K | a | 139.6 | Unit "A" | a | 3.0 | 0.0 | 2.0 | 0.0 | 1.0 | 1215 | 775 | | | |
| | b | 133.7 | | b | 4.0 | 0.0 | 0.0 | 0.0 | 0.0 | 1120 | 788 | | | |

TABLE 5-continued

| | | | | | | | | | | | | | | |
|---|---|---|---|---|---|---|---|---|---|---|---|---|---|---|
| | | | | | TEST RESULT | | | | | | | | | |
| INOCULATION LEVEL - about 100 org/mL | | | | | CULTURE RESULTS | | | | | | | | | |
| | | Broth Control | | | Whole Blood (org/mL) | | PreFitt | PstFitt | | AS-1 Red Cells (org/mL) | | | | |
| | repl | (org/mL) | | repl | Pre-Hold | Pst-Hold | Day 1 | Day 1 | Day 7 | Day 14 | Day 21 | Day 28 | Day 35 | Day 42 |
| | c | 134.4 | | c | 2.0 | 0.0 | 4.0 | 0.0 | 5.0 | 1163 | 805 | | | |
| | | | Unit "B" | a | 2.0 | 1.0 | 0.0 | NA | 68 | tntc | conf | | | |
| | | | unfiltered | b | 0.0 | 0.0 | 1.0 | NA | 44 | tntc | conf | | | |
| | | | | c | 0.0 | 0.0 | 0.0 | NA | 48 | tntc | conf | | | |
| Pool L | a | 139.6 | Unit "A" | a | 3.0 | 2.0 | 2.0 | 0.0 | 2.0 | 987 | tntc | | | |
| | b | 133.7 | | b | 6.0 | 2.0 | 2.0 | 0.0 | 1.0 | 804 | tntc | | | |
| | c | 134.4 | | c | 2.0 | 2.0 | 7.0 | 0.0 | 2.0 | 881 | tntc | | | |
| | | | Unit "B" | a | 1.0 | 5.0 | 1.0 | NA | 99 | tntc | conf | | | |
| | | | unfiltered | b | 4.0 | 1.0 | 3.0 | NA | 111 | tntc | conf | | | |
| | | | | c | 7.0 | 2.0 | * | NA | 106 | tntc | conf | | | |

tntc - too numerous to count
conf - confluent growth
NA - Not Applicable
* - plate overgrown The foregoing Results Tables demonstrate that clinically significant amounts of microorganisms like Yersinia present in the red blood cell product at the time of collection can be either eliminated or significantly reduced by filtration in accordance with the invention.

At inoculation levels representative of asymptomatic or otherwise apparently healthy donors (see Results Tables 2 and 3), the microorganism-depleted condition created in accordance with the invention at the outset of the storage period persists for extended storage intervals of at least 42 days. Even at a higher symptomatic inoculation level of about 30 organisms per ml. (Results Table 4), the microorganism-depleted condition is observed after 28 days of post-filtration storage. At these inoculation levels, red blood cell products that were not filtered in accordance with the invention exhibited clinically significant amounts of Yersinia organisms by about the seventh day of storage and confluent growths of Yersinia organisms by the twenty-first day of storage.

Even at Yersinia inoculation levels that are more than 10 times that would be present in asymptomatic or otherwise apparently healthy donors (see Result Table 5), the beneficial results of the invention are observed during storage periods of at least seven days.

Various features of the invention are set forth in the following claims.

We claim:

1. A method of processing a blood product containing red blood cells to remove microorganisms prior to long term storage, the method comprising the steps of:

collecting the blood product containing red blood cells in a first container that forms a part of a sterile, closed blood collection system including a storage container, a first fluid path that leads into the storage container, the first fluid oath including a dry inline filter medium comprising a mass of synthetic fibers having an average fiber diameter of about 10 microns or less and a bulk density of about 0.7 gram per cubic centimeter or less, and a second fluid path that leads from the storage container to the first container and bypasses the filter medium, adding a storage solution to the blood product without wetting the filter medium, before conveying any of the blood product containing the storage solution from the first container into the storage container through the first fluid path and the filter medium, and before wetting the filter medium, refrigerating the blood product containing the storage solution in the first container together with the closed blood collection system to cool the blood product containing the storage solution and the dry inline filter medium to a temperature of about 3 to 5 degrees C., thereby creating a precooled blood product containing the storage solution and a precooled dry inline filter medium, only after both the blood product containing the storage solution and the dry inline filter medium have been cooled to a temperature of about 3 to 5 degrees C., conveying the precooled blood product containing the storage solution from the first container into the storage container through the first fluid path and the precooled filter medium to remove microorganisms from the precooled blood product, venting air from the storage container into the first container through the second fluid path that bypasses the filter medium, and after venting the air from the storage container, storing the filtered, microorganism-depleted blood product containing the storage solution in the storage container at a temperature of about 3 to 5 degrees C. for a period that exceeds twenty-four hours after filtration.

2. A method according to claim 1 and further including the step of transfusing the filtered, microorganism-depleted blood product at the end of the storage period.

* * * * *